United States Patent [19]

Willey et al.

[11] Patent Number: 5,405,413

[45] Date of Patent: Apr. 11, 1995

[54] BLEACHING COMPOUNDS COMPRISING ACYL VALEROLACTAM BLEACH ACTIVATORS

[75] Inventors: Alan D. Willey, Cincinnati; Michael E. Burns, West Chester; Shuichi Tsunetsugu, Forest Park, all of Ohio

[73] Assignee: The Procter & Gamble Co., Cincinnati, Ohio

[21] Appl. No.: 82,207

[22] Filed: Jun. 24, 1993

[51] Int. Cl.$^6$ ............ C11D 3/28; C11D 3/39; C11D 3/395; D06L 3/02
[52] U.S. Cl. .................... 8/111; 8/137; 252/102; 252/173; 252/174.12; 252/174.21; 252/186.39; 252/524; 252/542; 252/DIG. 14; 546/298
[58] Field of Search .......... 252/102, 186.39, 186.31; 546/298; 8/111, 137

[56] References Cited

U.S. PATENT DOCUMENTS

| | | | |
|---|---|---|---|
| 3,177,148 | 4/1965 | Bright et al. | 252/99 |
| 4,013,575 | 3/1977 | Castrantas | 252/104 |
| 4,207,199 | 6/1980 | Perner et al. | 252/174 |
| 4,545,784 | 10/1985 | Sanderson | 8/107 |
| 4,820,437 | 4/1989 | Akabane et al. | 252/102 |
| 4,931,562 | 6/1990 | Akabane et al. | 546/19 |
| 5,112,514 | 5/1992 | Bolkan et al. | 252/99 |
| 5,160,655 | 11/1992 | Donker | 252/95 |

FOREIGN PATENT DOCUMENTS

0257700A2  3/1988  European Pat. Off. ............ 252/102

OTHER PUBLICATIONS

Chem. Abs. CA88:169981y "N-acyllactams & N-octylthiones", Ishida, A., Japan Kokai 7805,160, Jan. 18, 1978, vol. 88, pp. 577, 1978.

Chem. Abs. CA108:187402w, vol. 108, 1988, "Manufacture of α-acyl derivatives of w–amino acid Lactams", Stehlicek, J., Czech. CS 239,425, Apr. 16, 1987.

Primary Examiner—Dennis Albrecht
Attorney, Agent, or Firm—Michael D. Jones; Jerry J. Yetter; Jacobus C. Rasser

[57] ABSTRACT

Laundry detergents and bleaching systems comprise acyl valerolactam bleach activators. The bleach activators are effective under mixed soil conditions, especially mixtures of hydrophobic and hydrophilic soils and stains.

9 Claims, No Drawings

BLEACHING COMPOUNDS COMPRISING ACYL VALEROLACTAM BLEACH ACTIVATORS

FIELD OF THE INVENTION

The present invention relates to laundry detergents and bleaching systems which comprise acyl valerolactam bleach activators.

BACKGROUND OF THE INVENTION

It has long been known that peroxygen bleaches are effective for stain and/or soil removal from fabrics, but that such bleaches are temperature dependent. At a laundry liquor temperature of 60° C., peroxygen bleaches are only partially effective. As the laundry liquor temperature is lowered below 60° C., peroxygen bleaches become relatively ineffective. As a consequence, there has been a substantial amount of industrial research to develop bleaching systems which contain an activator that renders peroxygen bleaches effective at laundry liquor temperatures below 60° C.

Numerous substances have been disclosed in the art as effective bleach activators. One widely-used bleach activator is tetraacetyl ethylene diamine (TAED). TAED provides effective hydrophilic cleaning especially on beverage stains, but has limited performance on dingy stains and body soils. Another type of activator, such as nonanoyloxybenzenesulfonate (NOBS) and other activators which generally comprise long chain alkyl moieties, is hydrophobic in nature and provides excellent performance on dingy stains. However, many of the hydrophobic activators developed thus far can promote damage to natural rubber parts used in certain washing machines and to natural rubber articles exposed to the activators. Because of these negative effects on natural rubber machine parts and articles, the selection of such detergent-added bleaching systems has been limited.

It has now been determined that in conventional bleaching systems, particularly those comprising a hydrophobic bleach activator and a source of hydrogen peroxide, the bleach activator undergoes perhydrolysis to form a peroxyacid bleaching agent. A by-product of the perhydrolysis reaction between such bleach activators and hydrogen peroxide is a diacylperoxide (DAP) species. It has now further been discovered that the DAP's derived from hydrophobic activators tend to be insoluble, poorly dispersible, oily materials which form a residue which can deposit on the natural rubber machine parts that are exposed to the laundry liquor. The oily DAP residue can form a film on the natural rubber parts and promote free radical and peroxide damage to the rubber, which eventually leads to failure of the part. This is particularly true of rubber parts which have prolonged exposure to the laundry liquor, such as sump hoses.

By the present invention, is has now been discovered that the class of bleach activators derived from acyl valerolactams forms peroxyacids upon perhydrolysis without the production of oily, harmful DAP's. Without intending to be limited by theory, it is believed that the bleach activators employed herein provide good cleaning performance with safety to natural rubber, since they do not expose the natural rubber machine parts or articles to DAP oxidation. Whatever the reason, natural rubber parts and articles remain substantially undamaged by the bleaching systems of the present invention.

By the present invention, it has also now been discovered the bleach activators of this invention provide dingy soil clean-up and enhanced nucleophilic and body soil removal. Furthermore, the bleaching systems and activators herein are effective at low concentration levels and at temperatures below 60° C. when used in the manner provided by this invention. In addition, the activators herein have better perhydrolysis speed and yield when compared to other lactam bleach activators, such as acyl caprolactam activators.

Accordingly, the present invention presents an effective, color-safe bleaching system which does not promote damage to natural rubber parts in washing machines or damage to natural rubber articles.

SUMMARY OF THE INVENTION

The present invention relates to acyl valerolactam bleach activators and their use in bleaching systems and laundry detergents. The valerolactams are selected from the group consisting of:

a)

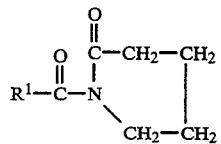

wherein $R^1$ is a substituted or unsubstituted, including saturated or unsaturated, alkyl or alkoxy group containing from about 1 to about 18 carbon atoms wherein the longest linear alkyl or alkoxy chain extending from and including the carbonyl carbon contains from about 2 to about 12 carbon atoms;

b)

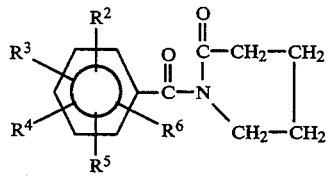

i.e., substituted and unsubstituted benzoyl valerolactams wherein substituents $R^2$, $R^3$, $R^4$, $R^5$, and $R^6$ are members selected from the group consisting of H, halogen, alkyl, alkoxy, alkoxyaryl, alkaryl, and alkaryloxy moieties having from about 1 to about 12 carbon atoms, preferably from about 3 to about 12 carbon atoms, and substituents having the structure:

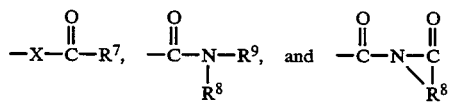

wherein $R^7$ is selected from the group consisting of H, alkyl, alkaryl, alkoxy, alkoxyaryl, alkaryloxy, and aminoalkyl; X is O, NH, or $NR^9$, wherein $R^9$ is H or a $C_1$–$C_4$ alkyl group; $R^8$ is an alkyl, cycloalkyl, or aryl group containing from 3 to 11 carbon atoms; and c) mixtures of a) and b).

In a preferred embodiment of structure a), $R^1$ is selected from the group consisting of alkyl or alkoxy units having from about 7 to about 11 carbon atoms, including heptyl, octyl, nonyl, decyl, undecyl, decenyl, 2,4,4-trimethylpentyl, 1-ethylpentyl, and mixtures thereof.

In a preferred embodiment of structure b), $R^2$, $R^3$, $R^4$, and $R^5$ are H and $R^6$ is selected from the group consisting of H, methyl, methoxy, ethyl, ethoxy, propyl, propoxy, isopropyl, isopropoxy, butyl, tert-butyl, butoxy, tert-butoxy, pentyl, pentoxy, hexyl, hexoxy, Cl, and $NO_2$. In still another preferred embodiment, $R^2$, $R^3$, $R^4$ are H, and $R^5$ and $R^6$ are members selected from the group consisting of methyl, methoxy, and Cl.

The invention also relates to bleaching systems and laundry detergents comprising the bleach activators. Said bleaching system comprises:

A) at least about 0.1%, preferably from about 1% to about 75%, by weight of bleaching system, of a peroxygen bleaching compound capable of yielding hydrogen peroxide in an aqueous solution;

B) at least about 0.1%, preferably from about 0.1% to about 50%, by weight, of one or more acyl valerolactam bleach activators selected from the group consisting of:

a)

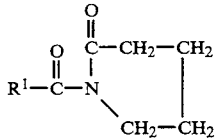

wherein $R^1$ is as defined above;

b)

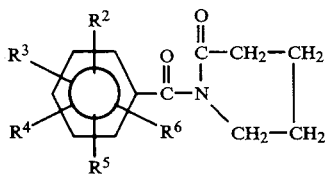

wherein $R^2$, $R^3$, $R^4$, $R^5$, and $R^6$ are as defined above; and c) mixtures of a) and b).

The peroxygen bleaching compound can be any peroxide source, and is preferably a member selected from the group consisting of sodium perborate monohydrate, sodium perborate tetrahydrate, sodium pyrophosphate peroxyhydrate, urea peroxyhydrate, sodium percarbonate, sodium peroxide and mixtures thereof. Highly preferred peroxygen bleaching compounds are selected from the group consisting of sodium perborate monohydrate, sodium perborate tetrahydrate, sodium percarbonate and mixtures thereof. The most highly preferred peroxygen bleaching compound is sodium percarbonate.

The invention also encompasses laundry compositions in granular, paste, liquid, or bar form which comprise at least about 0.1% of the aforesaid bleaching system together with at least about 1% of conventional detergent ingredients which are present in the composition at the levels indicated hereinafter.

The acyl valerolactams herein can also be used in combination with other bleach activators, such as N-acyl caprolactams, tetraacetyl ethylene diamine, alkanoxybenzenesulfonates, including nonanoyloxybenzenesulfonate, benzoxazin-type bleach activators, and peroxyacid agents and activators having amide moieties. Preferably, if using an automatic washing machine equipped with natural rubber parts or if washing articles comprising natural rubber, the amount of alkanoxybenezenesulfonates used in combination with the activators of this invention should be kept at a minimum.

The bleaching method herein is preferably conducted with agitation of the fabrics with an aqueous liquor containing the aforesaid bleaching system at levels from about 50 ppm to about 27,500 ppm. The method can be carried out at any desired washing temperature, even at temperatures below about 60° C., and is readily conducted at temperatures in the range of from about 5° C. to about 45° C. The method can be conducted conveniently using a composition which is in bar form, but can also be conducted using granules, flakes, powders, pastes, liquids and the like.

The aqueous laundry liquor typically comprises at least about 300 ppm of conventional detergent ingredients, as well as at least about 25 ppm of the bleaching compound and at least about 25 ppm of the bleach activator. Preferably, the liquor comprises from about 900 ppm to about 20,000 ppm of conventional detergent ingredients, from about 100 ppm to about 25,000 ppm of the bleaching compound and from about 100 ppm to about 2,500 ppm of the bleach activator. The conventional detergent ingredients and bleaching system will typically be combined into a detergent composition such as a granular laundry detergent or laundry detergent bar.

The conventional detergent ingredients employed in said method and in the compositions herein comprise from about 1% to about 99.8%, preferably from about 5% to about 80%, of a detersive surfactant. Optionally, the detergent ingredients comprise from about 5% to about 80% of a detergent builder. Other optional detersive adjuncts can also be included in such compositions at conventional usage levels.

All percentages, ratios, and proportions herein are by weight, unless otherwise specified. All documents cited are incorporated herein by reference.

DETAILED DESCRIPTION OF THE INVENTION

The bleaching system employed in the present invention provides effective and efficient surface bleaching of fabrics which thereby removes stains and/or soils from the fabrics. The bleaching system is particularly efficient at cleaning concentrated soil loads, especially mixtures of hydrophobic and hydrophilic soils. Hydrophobic soils are generally associated with nucleophilic, lipid and protein-based soils and stains, such as body soils, blood, etc., but are also effective on so-called "dingy soils". Dingy soils are those that build up on textiles after numerous cycles of usage and washing, and result in a gray or yellow tint on white fabrics. Hydrophilic soils include food and beverage stains. Further, the bleaching system is safe to natural rubber machine pans and articles.

The bleaching mechanism and, in particular, the surface bleaching mechanism are not completely understood. However, it is generally believed that the bleach activator undergoes nucleophilic attack by a perhydroxide anion, which is generated from the hydrogen peroxide evolved by the peroxygen bleaching compound, to form a peroxycarboxylic acid. This reaction is commonly referred to as perhydrolysis. It is also believed, that the bleach activators within this invention can render peroxygen bleaches more efficient even at laundry liquor temperatures wherein bleach activators are not necessary to activate the bleach, i.e., above about 60° C. Therefore, with bleach systems of the invention, less peroxygen bleach is required to achieve the same level of surface bleaching performance as is obtained with the peroxygen bleach alone.

The components of the bleaching system herein comprise the bleach activator and the peroxide source, as described hereinafter.

Bleach Activators

Methods of making acyl valerolactams are illustrated by laboratory syntheses included in Examples I and II.

Preferred valerolactams of structure a) include those wherein the $R^1$ moiety is selected from alkyl and alkoxy groups containing from about 7 to about 11 carbon atoms. Examples of preferred valerolactams include octanoyl valerolactam, nonanoyl valerolactam, decanoyl valerolactam, undecenoyl valerolactam, 3,5,5-trimethylhexanoyl valerolactam, 2-ethylhexanoyl valerolactam, isononanoyl valerolactam and mixtures thereof. Highly preferred valerolactams of structure a) include nonanoyl valerolactam, isononanoyl valerolactam, and 2-ethyhexanoyl valerolactam.

Preferred valerolactams of structure b) include benzoyl valerolactam, substituted benzoyl valerolactam, including alkaryl and alkoxyaryl valerolactams wherein the alkaryl or alkoxyaryl moiety contains from about 3 to about 12 carbon atoms, terephthaloyl divalerolactam, and mixtures thereof. Examples of substituted benzoyl valerolactams include methylbenzoyl valerolactam, ethylbenzoyl valerolactam, ethoxybenzoyl valerolactam, propylbenzoyl valerolactam, propoxybenzoyl valerolactam, isopropylbenzoyl valerolactam, isopropoxybenzoyl valerolactam, butylbenzoyl valerolactam, butoxybenzoyl valerolactam, tertbutylbenzoyl valerolactam, tertbutoxybenzoyl valerolactam, pentylbenzoyl valerolactam, pentoxybenzoyl valerolactam, hexylbenzoyl valerolactam, hexoxybenzoyl valerolactam, 2,4,6-trichlorobenzoyl valerolactam, pentafluorobenzoyl valerolactam, dichlorobenzoyl valerolactam, dimethoxybenzoyl valerolactam, 4-nitrobenzoyl valerolactam, 3-chlorobenzoyl valerolactam, 4-chlorobenzoyl valerolactam, 2,4-dichlorobenzoyl valerolactam, terephthaloyl divalerolactam, and mixtures thereof. Highly preferred valerolactams of structure b) include benzoyl valerolactam, 3-chlorobenzoyl valerolactam, and 4- nitrobenzoyl valerolactam.

The bleaching system comprises at least about 0.1%, preferably from about 0.1% to about 50%, more preferably from about 1% to about 30%, most preferably from about 3% to about 25%, by weight, of one or more acyl valerolactam bleach activators. In highly preferred embodiments, the bleaching system comprises percarbonate and a bleach activator selected from the group consisting of benzoyl valerolactam, nonanoyl valerolactam, isononanoyl valerolactam, 2-ethylhexanoyl valerolactam, 3-chlorobenzoyl valerolactam, and 4-nitrobenzoyl valerolactam.

When the activators are used, optimum surface bleaching performance is obtained with washing solutions wherein the pH of such solution is between about 7 and 10.5, preferably between about 8.5 and 10.5, most preferably about 9.5 to about 10.5, in order to facilitate the perhydrolysis reaction. Such pH can be obtained with substances commonly known as buffering agents, which are optional components of the bleaching systems herein.

The Peroxygen Bleaching Compound

The peroxygen bleaching compounds useful herein are those capable of yielding hydrogen peroxide in an aqueous liquor. These compounds are well known in the art and include hydrogen peroxide and the alkali metal peroxides, organic peroxide bleaching compounds such as urea peroxide, and inorganic persalt bleaching compounds, such as the alkali metal perborates, percarbonates, perphosphates, and the like. Mixtures of two or more such bleaching compounds can also be used, if desired.

Preferred peroxygen bleaching compounds include sodium perborate, commercially available in the form of mono-, tri-, and tetra-hydrate, sodium pyrophosphate peroxyhydrate, urea peroxyhydrate, sodium peroxide, and sodium percarbonate. Particularly preferred are sodium perborate tetrahydrate, sodium perborate monohydrate and sodium percarbonate. Sodium percarbonate is especially preferred because it is very stable during storage and yet still dissolves very quickly in the bleaching liquor. It is believed that such rapid dissolution results in the formation of higher levels of percarboxylic acid and, thus, enhanced surface bleaching performance.

Highly preferred percarbonate can be in uncoated or coated form. The average particle size of uncoated percarbonate ranges from about 400 to about 1200 microns, most preferably from about 400 to about 600 microns. If coated percarbonate is used, the preferred coating materials include mixtures of carbonate and sulphate, silicate, borosilicate, or fatty carboxylic acids.

The bleaching system comprises at least about 0.1%, preferably from about 1% to about 75%, more preferably from about 3% to about 40%, most preferably from about 3% to about 25%, by weight, of said peroxygen bleaching compound capable of yielding hydrogen peroxide in an aqueous solution.

The weight ratio of bleach activator to peroxygen bleaching compound in the bleaching system typically ranges from about 2:1 to 1:5. In preferred embodiments, the ratio ranges from about 1:1 to about 1:3.

The bleach activator/bleaching compound systems herein are useful per se as bleaches. However, such bleaching systems are especially useful in compositions which can comprise various detersive adjuncts such as surfactants, builders, enzymes, and the like as disclosed hereinafter. Such laundry detergent compositions comprise at least about 0.1%, preferably from about 1% to about 50%, of the bleaching system and at least about 1%, preferably from about 50% to about 99.9%, of conventional detergent ingredients.

Detersive Surfactant

The amount of detersive surfactant included in the fully formulated detergent compositions afforded by the present invention can vary from about 1% to about 99.8%, by weight of the detergent ingredients, depending upon the particular surfactants used and the effects desired. Preferably, the detersive surfactants comprise from about 5% to about 80%, by weight of the detergent ingredients.

The detersive surfactant can be nonionic, anionic, ampholytic, zwitterionic, or cationic. Mixtures of these surfactants can also be used. Preferred detergent compositions comprise anionic detersive surfactants or mixtures of anionic surfactants with other surfactants, especially nonionic surfactants.

Nonlimiting examples of surfactants useful herein include the conventional $C_{11}-C_{18}$ alkyl benzene sulfonates and primary, secondary, and random alkyl sulfates, the $C_{10}-C_{18}$ alkyl alkoxy sulfates, the $C_{10}-C_{18}$ alkyl polyglycosides and their corresponding sulfated polyglycosides, $C_{12}-C_{18}$ alpha-sulfonated fatty acid esters, $C_{12}-C_{18}$ alkyl and alkyl phenol alkoxylates (especially ethoxylates and mixed ethoxy/propoxy), $C_{12}-C_{18}$ betaines and sulfobetaines ("sultaines"), $C_{10}-C_{18}$ amine oxides, and the like. Other conventional useful surfactants are listed in standard texts.

One particular class of adjunct nonionic surfactants especially useful herein comprises the polyhydroxy fatty acid amides of the formula:

$$R^2-\underset{\underset{O}{\|}}{C}-\underset{\underset{R^1}{|}}{N}-Z \quad (I)$$

wherein: $R^1$ is H, $C_1-C_8$ hydrocarbyl, 2-hydroxyethyl, 2-hydroxypropyl, or a mixture thereof, preferably $C_1-C_4$ alkyl, more preferably $C_1$ or $C_2$ alkyl, most preferably $C_1$ alkyl (i.e., methyl); and $R^2$ is a $C_5-C_{32}$ hydrocarbyl moiety, preferably straight chain $C_7-C_{19}$ alkyl or alkenyl, more preferably straight chain $C_9-C_{17}$ alkyl or alkenyl, most preferably straight chain $C_{11}-C_{19}$ alkyl or alkenyl, or mixture thereof, and Z is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —CH$_2$—(CHOH)$_n$—CH$_2$OH, —CH(CH$_2$OH)—(CHOH)$_{n-1}$—CH$_2$H, —CH$_2$—(CHOH)$_2$(CHOR')(CHOH)—CH$_2$OH, where n is an integer from 1 to 5, inclusive, and R' is H or a cyclic mono- or poly-saccharide, and alkoxylated derivatives thereof. Most preferred are glycityls wherein n is 4, particularly —CH$_2$—(CHOH)$_4$—CH$_2$OH.

In Formula (I), $R^1$ can be, for example, N-methyl, N-ethyl, N-propyl, N-isopropyl, N-butyl, N-isobutyl, N-2-hydroxy ethyl, or N-2-hydroxy propyl. For highest sudsing, $R^1$ is preferably methyl or hydroxyalkyl. If lower sudsing is desired, $R^1$ is preferably $C_2-C_8$ alkyl, especially n-propyl, iso-propyl, n-butyl, iso-butyl, pentyl, hexyl and 2-ethyl hexyl.

$R^2$—CO—N< can be, for example, cocamide, stearamide, oleamide, lauramide, myristamide, capricamide, palmitamide, tallowamide, etc.

Detergent Builders

Optional detergent ingredients employed in the present invention contain inorganic and/or organic detergent builders to assist in mineral hardness control. If used, these builders comprise from about 5% to about 80% by weight of the detergent compositions.

Inorganic detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck, available from Hoechst under the trademark "SKS"; SKS-6 is an especially preferred layered silicate builder.

Carbonate builders, especially a finely ground calcium carbonate with surface area greater than 10 m$^2$/g, are preferred builders that can be used in granular compositions. The density of such alkali metal carbonate built detergents can be in the range of 450-850 g/l with the moisture content preferably below 4%. Examples of carbonate builders are the alkaline earth and alkali metal carbonates as disclosed in German Patent Application No. 2,321,001 published on Nov. 15, 1973.

Aluminosilicate builders are especially useful in the present invention. Preferred aluminosilicates are zeolite builders which have the formula:

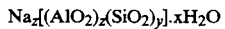

$$Na_z[(AlO_2)_z(SiO_2)_y]\cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), and Zeolite X. Preferably, the aluminosilicate has a particle size of about 0.1-10 microns in diameter.

Organic detergent builders suitable for the purposes of the present invention include, but are not restricted to, a wide variety of polycarboxylate compounds, such as ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987.

Other useful detergent builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, suetinit acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are preferred polycarboxylate builders that can also be used in granular compositions, especially in combination with zeolite and/or layered silicate builders.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Optional Detersive Adjuncts

As a preferred embodiment, the conventional detergent ingredients employed herein can be selected from typical detergent composition components such as detersive surfactants and detergent builders. Optionally, the detergent ingredients can include one or more other detersive adjuncts or other materials for assisting or enhancing cleaning performance, treatment of the substrate to be cleaned, or to modify the aesthetics of the detergent composition. Usual detersive adjuncts of detergent compositions include the ingredients set forth in U.S. Pat. No. 3,936,537, Baskerville et al. Adjuncts which can also be included in detergent compositions employed in the present invention, in their conventional an-established levels for use (generally from 0% to about 20% of the detergent ingredients, preferably from about 0.5% to about 10%), include enzymes, especially proteases, lipases and cellulases, color speckles, suds boosters, suds suppressors, antitarnish and/or anticorrosion agents, soil-suspending agents, soil release agents, dyes, fillers, optical brighteners, germicides, alkalinity sources, hydrotropes, antioxidants, enzyme stabilizing agents, perfumes, solvents, solubilizing agents, clay soil removal/anti-redeposition agents, polymeric dispersing agents, processing aids, fabric softening components such as smectite clays, static control agents, etc.

Bleach systems optionally, but preferably, will also comprise a chelant which not only enhances bleach stability by scavenging heavy metal ions which tend to decompose bleaches, but also assists in the removal of polyphenolic stains such as tea stains, and the like. Various chelants, including the aminophosphonates, available as DEQUEST from Monsanto, the nitrilotri acetates, the hydroxyethyl-ethyl enedi amine triacetates, and the like, are known for such use. Preferred biodegradable, non-phosphorus chelants include ethylenediamine disuccinate ("EDDS"; see U.S. Pat. No. 4,704,233, Hartman and Perkins), ethylenediamine-N,N'-diglutamate (EDDG) and 2-hydroxypropylenediamine-N,N'-disuccinate (HPDDS) compounds. Such chelants can be used in their alkali or alkaline earth metal salts, typically at levels from about 0.1% to about 10% of the present compositions.

Optionally, the detergent compositions employed herein can comprise, in addition to the bleaching system of the present invention, one or more other conventional bleaching agents, activators, or stabilizers. In general, the formulator will ensure that the bleach compounds used are compatible with the detergent formulation. Conventional tests, such as tests of bleach activity on storage in the presence of the separate or fully-formulated ingredients, can be used for this purpose.

Specific examples of optional bleach activators for incorporation in this invention include tetraacetyl ethylene diamine (TAED), N-acyl caprolactams, alkanoyloxybenzenesulfonates, including nonanoyloxybenzenesulfonate and benzoyloxybenzenesulfonate, the benzoxazin-type bleaching activators disclosed in U.S. Pat. No. 4,966,723, Hodge et at, issued Oct. 30, 1990, and the peroxyacid agents and activators having amide moieties disclosed in U.S. Pat. No. 4,634,551, Burns et at, issued Jan. 6, 1987. Such bleaching compounds and agents can be optionally included in detergent compositions in their conventional art-established levels of use, generally from 0% to about 15%, by weight of detergent composition.

Bleaching activators of the invention are especially useful in conventional laundry detergent compositions such as those typically found in granular detergents or laundry bars. U.S. Pat. No. 3,178,370, Okenfuss, issued Apr. 13, 1965, describes laundry detergent bars and processes for making them. Philippine Patent 13,778, Anderson, issued Sep. 23, 1980, describes synthetic detergent laundry bars. Methods for making laundry detergent bars by various extrusion methods are well known in the art.

Perhydrolysis Speed and Yield

The activators herein have better perhydrolysis speed and yield when compared to other lactam derived bleach activators. For example, after approximately five minutes, a solution of nonanoyl valerolactam generates approximately 95% of the theoretical yield of peracid. In comparison, after approximately five minutes, an identical solution of nonanoyl caprolactam generates approximately 35% of the theoretical yield of peracid. After 15 minutes, the nonanoyl caprolactam solution generates approximately 68% of the theoretical yield of peracid. Accordingly, the user can expect better bleaching performance at shorter wash times with the valerolactam activators.

The comparison is made using standard peracid titration procedures. The activator is dispersed in a detergent solution. At specific time intervals, samples of the solution are taken and added to a mixture of acetic acid, water, and ice to quench the perhydrolysis reaction. A quantity of potassium iodide is added to the sample giving the sample a brown color. The resulting solution is titrated with thiosulphate until the color is removed. From the known quantity of thiosulphate used in the titration, the amount of peracid can be determined.

Liquid Bleaches

The bleach activators of this invention are also useful in liquid bleach compositions. Therefore, in accordance with one aspect of the invention, a stable aqueous liquid bleach is provided. In a preferred embodiment, the liquid bleaches comprise a liquid valerolactam such as decanoyl valerolactam or nonanoyl valerolactam which is most preferably emulsified in the peroxide liquid composition. Such liquid bleaches comprise:

A) from about 1% to about 25%, more preferably from about 3% to about 12%, most preferably from about 5% to about 10%, by weight, of a (solid or, preferably, liquid) valerolactam bleach activator selected from the group consisting of:

a)

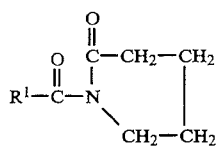

wherein R₁ is as defined above;

b)

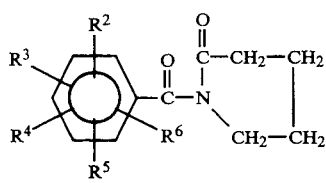

wherein $R^2$, $R^3$, $R^4$, $R^5$, and $R^6$ are as defined above; and c) mixtures of a) and b);

B) from about 0.1% to about 10%, more preferably from about 0.3% to about 7%, most preferably from about 0.5% to about 5%, by weight, of a peroxygen bleaching compound comprising hydrogen peroxide or which is capable of yielding hydrogen peroxide in an aqueous solution.

Optionally, the liquid bleach composition can further comprise from about 1% to about 20%, preferably from about 5% to about 15%, by weight, of a phase stabilizer and from about 0.001% to about 2%, preferably from about 0.05% to about 1%, by weight, of a chelating agent. The balance of the liquid bleach composition is water.

The liquid peroxide-containing bleach is formulated in the acid pH range for stability. In-use in a laundering operation, the bleach is added to a laundry liquor which typically has a pH in the base range, i.e., 9.5-13, which then destabilizes the peroxide to perform its bleaching function.

Nonionic Surfactant

The liquid bleach compositions of the invention, optionally, but preferably, include a nonionic surfactant as a phase stabilizer to facilitate maintenance of its continuous isotropic state. To this end, several nonionic surfactants are particularly useful. Suitable nonionic surfactants include the polyethylene oxide condensates of alkyl phenols, e.g., the condensation products of alkyl phenols having an alkyl group containing from about 6 to 15 carbon atoms, in either a straight chain or branched chain configuration, with from about 3 to 20 moles of ethylene oxide per mole of alkyl phenol.

Other nonionic surfactants which function as suitable phase stabilizers are the water-soluble and water-dispersible condensation products of aliphatic alcohols containing from 8 to 22 carbon atoms, in either straight chain or branched configuration, with from 3 to 20 moles of ethylene oxide per mole of alcohol. Still other nonionic surfactants include semi-polar nonionic surfactants such as water-soluble amine oxides containing one alkyl moiety of from about 10 to 18 carbon atoms and two moieties selected from about 1 to about 3 carbon atoms; water-soluble phosphine oxides containing one alkyl moiety of about 10 to 18 carbon atoms and two moieties selected from the group consisting of alkyl groups and hydroxyalkyl groups containing from about 1 to 3 carbon atoms; and water-soluble sulfoxides containing only alkyl moiety of from about 10 to 18 carbon atoms and a moiety selected from the group consisting of alkyl and hydroxyalkyl moieties of from about 1 to 3 carbon atoms.

Preferred nonionic surfactants are of the formula $R^1(OC_2H_4)_nOH$, wherein $R^1$ is a $C_8$–$C_{16}$ alkyl group of $C_8$–$C_{12}$ alkyl phenyl group, and n is from 3 to about 20. Particularly preferred are condensation products of $C_9$–$C_{15}$ alcohols with from about 5 to about 20 moles of ethylene oxide per mole of alcohol. The most preferred nonionic of this type is an alkyl ethoxylate having from about 9 to 11 carbon atoms and an average degree of ethoxylation of about 10 which is available from Shell Oil Co. under the product name of NEODOL 91-10.

The liquid bleach composition will generally comprise from about 1% to about 20%, preferably from about 5% to about 15%, by weight, of the nonionic surfactant phase stabilizer.

With the aforementioned chelating agent and phase stabilizer, i.e. nonionic surfactant, the stable aqueous liquid bleach composition in accordance with the invention can be produced. The resulting liquid bleach composition has a relatively low viscosity which renders it more pourable and therefore, more convenient for users especially when the composition is used as an additive. The viscosity of the present liquid bleach is preferably in a range from about 10 to about 500 cps, more preferably from about 10 to about 300 cps, and most preferably from about 10 to 100 cps.

pH Adjusting Agent

It has been found that optimum stability of the liquid peroxygen bleaches is achieved when the aqueous liquid bleach has a pH in range from about 2 to about 7, more preferably from about 3 to about 5, and most preferably from about 3.5 to about 4.5. For purposes of achieving such pH's in the present stable aqueous liquid bleach composition, a pH adjusting agent may optionally be included. It is a well known technique to use pH adjusting agents to alter aqueous solutions such as the present liquid bleach, to the desired pH.

Typical pH adjusting agents can be either of the acid type or of the base type. Acidic pH adjusting agents are designed to compensate for the presence of other highly alkaline materials land include organic and inorganic acids, acid mixtures and acid salts. Non-limiting examples of such acidic pH adjusting agents include citric acid, glycolic acid, phosphoric acid, lauric acid and mixtures thereof. Representative examples of alkaline pH adjusting agents include but not limited to sodium hydroxide, salts of phosphates, citrates and mixtures thereof.

In addition to the materials described above, the liquid bleach may also include perfumes colorants, brighteners, viscosity adjusters such as thickeners, and other conventional components typically used in detergent compositions, if compatible.

The liquid bleach of the invention can be produced by a wide variety of processes. While not intending to be limiting, the most economical and easiest manner in which the liquid bleach can be produced is to simply disperse all of the preferred components in water. As those skilled in the art will appreciate, it may be desirable to disperse certain components in water before others. This offers an inexpensive way to produce the present liquid bleach composition.

In accordance with another aspect of the invention, a method of bleaching fabrics comprises the step of contacting fabrics with a diluted aqueous solution of the liquid composition of the invention. Another method contemplated by the invention involves laundering soiled clothes, using the liquid bleach composition as an additive. The method comprises the steps of contacting fabrics with an effective amount of a detergent composition in combination with an effective amount of a stable aqueous liquid bleach composition. In practicing these methods, the stable aqueous liquid bleach compositions of the present invention can be used in widely varying concentrations depending on the particular application involved but are generally utilized in an amount sufficient to provide from about 1.0 ppm to about 50 ppm available oxygen from the peracid in solution.

The following examples are given to further illustrate the present invention, but are not intended to be limiting thereof

EXAMPLE I

Synthesis of benzoyl valerolactam—To a 500 ml flask equipped with a reflux condenser, overhead stirrer, and addition funnel is charged 0.12 moles of valerolactam, 0.15 moles of triethylamine and 150 ml of toluene. The solution is heated to 80° C. and a solution of 0.12 moles of benzoyl chloride dissolved in 50 ml of toluene is added over 20 minutes. The mixture is refluxed for six hours with stirring, cooled, and filtered. The filtrate is concentrated under vacuum to a brown solid which is recrystallized from toluene to yield 0.092 moles of benzoyl valerolactam. 1H NMR analysis shows the product to be greater than 95% pure. Analysis: $^1$H NMR (ppm)- 1.9(M, 4H); 2.5(t, 2H);3.7(t, 2H);7.4(M, 5H). IR (cm$^1$)- 2925, 2856, 1686, 1673, 1458, 1287.

EXAMPLE II

Synthesis of nonanoyl valerolactam—To a 5 liter flask equipped with a reflux condenser, argon sweep, addition funnel, and overhead stirrer is charged 2.5 moles of valerolactam, 2.75 moles of triethylamine, and 2 liters of toluene. The solution is heated to reflux, and 2.5 moles of nonanoyl chloride is added over 1.5 hours. The mixture is refluxed with stirring for 6 hours cooled, and filtered. The filtrate is concentrated under vacuum, and the resultant oil is distilled at 162° C. and approximately 1 mm Hg to yield 1.6 moles of nonanoyl valerolactam. NMR analysis shows the product to be greater than 95% pure. Analysis: $^1$H NMR (ppm)-0.9(t, 3H); 1.3(M, 10H); 1.6(M, 2H); 1.9(M, 4H); 2.6(M, 2H); 2.9(t, 2H); 3.7(M, 2H). IR (cm$^1$)-2927, 2857, 1697, 1461, 1377, 1291, 1197, 1161.

EXAMPLE III

A granular detergent composition is prepared comprising the following ingredients.

| Component | Weight % |
| --- | --- |
| C$_{12}$ linear alkyl benzene sulfonate | 22 |
| Phosphate (as sodium tripolyphosphate) | 20 |
| Sodium carbonate | 10 |
| Sodium silicate | 3 |
| Sodium percarbonate* | 20 |
| Ethylenediamine disuccinate chelant (EDDS) | 0.4 |
| Sodium sulfate | 5.5 |
| Nonanoyl valerolactam | 10 |

-continued

| Component | Weight % |
| --- | --- |
| Minors, filler** and water | Balance to 100% |

*Average particle size of 400 to 1200 microns.
**Can be selected from convenient materials such as CaCO$_3$, talc, clay, silicates, and the like.

An aqueous crutcher mix of heat and alkali stable components of the detergent composition is prepared and spray-dried. The other ingredients are admixed therewith so that they contain the ingredients tabulated at the levels shown.

The detergent granules with bleaching system are added together with a 6 lb. (2.7 kg) load of fabrics to a Sears KENMORE washing machine. Actual weight of the detergent composition is taken to provide a 1500 ppm concentration of the detergent composition in the 17 gallon (65 l) water-fill machine. The water used has 7 grains/gallon hardness and a pH of 7 to 7.5 prior to (about 9 to about 10.5 after) addition of the detergent composition. The fabrics are laundered at 35° C. (95° F.) for a full cycle (12 min.) and rinsed at 21° C. (70° F.).

At the end of the last rinse cycle, the test swatches are dried in a dryer. Tristimulus meter readings (L,a,b) are then determined for each test swatch. Whiteness performance in terms of Hunter Whiteness Values (W) is then calculated according to the following equation:

$$W=(7L^2-40Lb)/700$$

The higher the value for W, the better the whiteness performance. In the above test, fabrics exposed to the bleaching system display significantly improved whiteness after laundering compared with fabrics which have not been exposed to the bleaching system of the invention.

EXAMPLE IV

A granular detergent is prepared by a procedure identical to that of Example III, with the exception that 20% benzoyl valerolactam is substituted for the nonanoyl valerolactam bleach activator. The laundering method of Example III is repeated. In the test, all fabrics display significantly improved whiteness after laundering compared with fabrics which have not been exposed to the bleaching system of the invention.

EXAMPLE V

A granular detergent is prepared by a procedure identical to that of Example III, with the exceptions that 10% 4-nitrobenzoyl valerolactam is substituted for the nonanoyl valerolactam bleach activator. The laundering method of Example III is repeated. In the test, all fabrics display significantly improved whiteness after laundering compared with fabrics which have not been exposed to the bleaching system of the invention.

EXAMPLE VI

A granular detergent is prepared by a procedure identical to that of Example III, with the exceptions that 5% isononanoyl valerolactam is substituted for the nonanoyl valerolactam bleach activator and the amount of sodium percarbonate is 10%. The laundering method of Example III is repeated. In the test, all fabrics display significantly improved whiteness after laundering compared with fabrics which have not been exposed to the bleaching system of the invention.

EXAMPLE VII

A granular detergent is prepared by a procedure identical to that of Example III, with the exceptions that 20% 3-chlorobenzoyl valerolactam is substituted for the nonanoyl valerolactam bleach activator and the amount of sodium percarbonate is 20%. The laundering method of Example III is repeated. In the test, all fabrics display significantly improved whiteness after laundering compared with fabrics which have not been exposed to the bleaching system of the invention.

EXAMPLE VIII

A granular detergent is prepared by a procedure identical to that of Example III, with the single exception that 15% of a 1:1 mixture of benzoyl valerolactam and nonanoyl valerolactam is substituted for the nonanoyl valerolactam bleach activator. The laundering method of Example III is repeated. In the test, all fabrics display significantly improved whiteness after laundering compared with fabrics which have not been exposed to the bleaching system of the invention.

EXAMPLE IX

A granular detergent is prepared by a procedure identical to that of Example III, with the single exception that 15% of a 1:1 mixture of benzoyl valerolactam and nonanoyloxybenzenesulfonate is substituted for the nonanoyl valerolactam bleach activator. The laundering method of Example III is repeated. In the test, all fabrics display significantly improved whiteness after laundering compared with fabrics which have not been exposed to the bleaching system of the invention.

EXAMPLE X

A granular detergent is prepared by a procedure identical to that of Example III, with the single exception that 15% of a 1:1 mixture of 4-ethylbenzoyl valerolactam and a benzoxazin-type bleach activator is substituted for the nonanoyl valerolactam bleach activator. The laundering method of Example III is repeated. In the test, all fabrics display significantly improved whiteness after laundering compared with fabrics which have not been exposed to the bleaching system of the invention.

EXAMPLE XI

A granular detergent is prepared by a procedure identical to that of Example III, with the single exception that an equivalent amount of decanoyl valerolactam is substituted for the nonanoyl valerolactam bleach activator. The laundering method of Example III is repeated. In the test, all fabrics display significantly improved whiteness after laundering compared with fabrics which have not been exposed to the bleaching system of the invention.

EXAMPLE XII

A granular detergent composition is prepared comprising the following ingredients.

| Component | Weight % |
| --- | --- |
| Anionic alkyl sulfate | 7 |
| Nonionic surfactant | 5 |
| Zeolite A (0.1–10 micron) | 10 |
| Trisodium citrate | 2 |
| SKS-6 silicate builder | 10 |
| Acrylate maleate polymer | 4 |
| Nonanoyl valerolactam | 10 |
| Sodium percarbonate | 25 |
| Sodium carbonate | 5 |
| Ethylenediamine disuccinate chelant (EDDS) | 0.4 |
| Suds suppressor | 2 |
| Enzymes* | 1.5 |
| Soil release agent | 0.2 |
| Minors, filler** and water | Balance to 100% |

*1:1:1 mixture of protease, lipase, and cellulase.
**Can be selected from convenient materials such as CaCO$_3$, talc, clay, silicates, and the like.

An aqueous crutcher mix of heat and alkali stable components of the detergent composition is prepared and spray-dried. The other ingredients are admixed therewith so that they contain the ingredients tabulated at the levels shown.

The detergent granules with bleaching system are added together with a 2.7 kg load of fabrics to an automatic washing machine. Actual weights of detergent and ester compositions are taken to provide a 5000 ppm concentration of the detergent composition in the 17 liter (4.5 gallon) water-fill machine. The water used has 10 grains/gallon hardness and a pH of 7 to 7.5 prior to (about 9 to about 10.5 after) addition of the detergent composition.

The fabrics are laundered at 40° C. (104° F.) for a full cycle (40 min.) and rinsed at 21° C. (70° F.).

At the end of the last rinse cycle, the test swatches are dried in a dryer. Tristimulus meter readings (L,a,b) are then determined for each test swatch. Whiteness performance in terms of Hunter Whiteness Values (W) is then calculated according to the following equation:

$$W=(7L^2-40Lb)/700$$

The higher the value for W, the better the whiteness performance. In the above test, fabrics exposed to the bleaching system display significantly improved whiteness after laundering compared with fabrics which have not been exposed to the bleaching system of the invention.

EXAMPLE XIII

A granular detergent is prepared by a procedure identical to that of Example XII, with the exception that 10% isononanoyl valerolactam is substituted for the nonanoyl valerolactam bleach activator. The laundering method of Example XII is repeated. In the test, all fabrics display significantly improved whiteness after laundering compared with fabrics which have not been exposed to the bleaching system of the invention.

EXAMPLE XIV

A granular detergent is prepared by a procedure identical to that of Example XII, with the exceptions that 10% 2-ethylhexanoyl valerolactam is substituted for the nonanoyl valerolactam bleach activator. The laundering method of Example XII is repeated. In the test, all fabrics display significantly improved whiteness after laundering compared with fabrics which have not been exposed to the bleaching system of the invention.

EXAMPLE XV

A granular detergent is prepared by a procedure identical to that of Example XII, with the exceptions that 15% benzoyl valerolactam is substituted for the nonanoyl valerolactam bleach activator and the amount of sodium percarbonate is 30%. The laundering method of Example XII is repeated. In the test, all fabrics display significantly improved whiteness after laundering compared with fabrics which have not been exposed to the bleaching system of the invention.

EXAMPLE XVI

A granular detergent is prepared by a procedure identical to that of Example XII, with the single exception that 15% of a 1:1 mixture of 4-chlorobenzoyl valerolactam and a benzoxazin-type bleach activator is substituted for the nonanoyl valerolactam bleach activator. The laundering method of Example XII is repeated. In the test, all fabrics display significantly improved whiteness after laundering compared with fabrics which have not been exposed to the bleaching system of the invention.

EXAMPLE XVII

A granular detergent is prepared by a procedure identical to that of Example XII, with the single exception that 15% of a 1:1 mixture of isonanoyl valerolactam and tetraacetyl ethylene diamine bleach activator is substituted for the nonanoyl valerolactam bleach activator. The laundering method of Example XII is repeated. In the test, all fabrics display significantly improved whiteness after laundering compared with fabrics which have not been exposed to the bleaching system of the invention.

EXAMPLE XVIII

A granular detergent is prepared by a procedure identical to that of Example XII, with the single exception that 15% of a 1:1 mixture of isononanoyl valerolactam and benzoyl caprolactam is substituted for the nonanoyl valerolactam bleach activator. The laundering method of Example XII is repeated. In the test, all fabrics display significantly improved whiteness after laundering compared with fabrics which have not been exposed to the bleaching system of the invention.

EXAMPLE XIX

A laundry bar suitable for hand-washing soiled fabrics is prepared comprising the following ingredients.

| Component | Weight % |
| --- | --- |
| $C_{12}$ linear alkyl benzene sulfonate | 30 |
| Phosphate (as sodium tripolyphosphate) | 7 |
| Sodium carbonate | 15 |
| Sodium pyrophosphate | 7 |
| Coconut monoethanolamide | 2 |
| Zeolite A (0.1–10 microns) | 5 |
| Carboxymethylcellulose | 0.2 |
| Polyacrylate (m.w. 1400) | 0.2 |
| Benzoyl valerolactam | 6.5 |
| Sodium percarbonate | 15 |
| Brightener, perfume | 0.2 |
| Protease | 0.3 |
| $CaSO_4$ | 1 |
| $MgSO_4$ | 1 |
| Water and Filler* | Balance to 100% |

*Can be selected from convenient materials such as $CaCO_3$, talc, clay, silicates, and the like.

Detergent laundry bar is extruded in conventional soap or detergent bar making equipment as commonly used in the art. Testing is conducted following the methods used in Example IV. In the test, fabrics exposed to the bleaching system display significantly improved whiteness after laundering compared with fabrics which have not been exposed to the bleaching system of the invention.

EXAMPLE XX

A laundry bar is prepared by a procedure identical to that of Example XIX, with the two exceptions that 15% of a 1:1 mixture of benzoyl valerolactam and nonanoyl valerolactam is substituted for the benzoyl valerolactam bleach activator, and the level of sodium percarbonate is increased to 20%. The laundering method of Example XIX is repeated. In the test, all fabrics display significantly improved whiteness after laundering compared with fabrics which have not been exposed to the bleaching system of the invention.

EXAMPLE XXI

A laundry bar is prepared by a procedure identical to that of Example XIX, with the two exceptions that 15% of a 1:1 mixture of isononanoyl valerolactam and 2,4-dichlorobenzoyl valerolactam is substituted for the benzoyl valerolactam bleach activator, and the level of sodium percarbonate is increated to 20%. The laundering method of Example XIX is repeated. In the test, all fabrics display significantly improved whiteness after laundering compared with fabrics which have not been exposed to the bleaching system of the invention.

EXAMPLE XXII

A laundry bar is prepared by a procedure identical to that of Example XIX, with the two exceptions that 15% of a 1:1 mixture of decanoyl valerolactam and benzoyl valerolactam is substituted for the benzoyl valerolactam bleach activator, and the level of sodium percarbonate is increated to 20%. The laundering method of Example XIX is repeated. In the test, all fabrics display significantly improved whiteness after laundering compared with fabrics which have not been exposed to the bleaching system of the invention.

EXAMPLE XXIII

A laundry bar is prepared by a procedure identical to that of Example XIX, with the two exceptions that an equivalent amount of butoxybenzoyl valerolactam is substituted for the benzoyl valero-lactam bleach activator, and the level of sodium percarbonate is increated to 20%. The laundering method of Example XIX is repeated. In the test, all fabrics display significantly improved whiteness after laundering compared with fabrics which have not been exposed to the bleaching system of the invention.

EXAMPLE XXIV

A bleaching system is prepared comprising the following ingredients.

| Component | Weight % |
| --- | --- |
| Nonanoyl valerolactam | 15 |
| Tetraacetyl ethylene diamine | 15 |
| Sodium percarbonate | 45 |
| Chelant (ethylenediamine disuccinate, EDDS) | 10 |
| Filler* and water | Balance to 100% |

*Can be selected from convenient materials such as $CaCO_3$, talc, clay, silicates, and the like.

Testing is conducted following the methods used in Example IV with the single exception that the an equivalent amount of the above bleaching system is substituted for the detergent composition used in Example IV. In the test, fabrics exposed to the bleaching system display significantly improved whiteness after laundering compared with fabrics which have not been exposed to the bleaching system of the invention.

EXAMPLE XXV

A bleaching system is prepared by a procedure identical to that of Example XXIV, with the exception that an equivalent amount of 4-butylbenzoyl valerolactam is substituted for the nonanoyl valerolactam bleach activator. The laundering method of Example XXIV is repeated. In the test, all fabrics display significantly improved whiteness after laundering compared with fabrics which have not been exposed to the bleaching system of the invention.

EXAMPLE XXVI

A bleaching system is prepared by a procedure identical to that of Example XXIV, with the exception that an equivalent amount of terephthaloyl divalerolactam is substituted for the nonanoyl valerolactam bleach activator. The laundering method of Example XXIV is repeated. In the test, all fabrics display significantly improved whiteness after laundering compared with fabrics which have not been exposed to the bleaching system of the invention.

While the compositions and processes of the present invention are useful in conventional laundering operations, it is to be understood that they are also useful in any cleaning system which involves low water:fabric ratios. One such system is disclosed in U.S. Pat. No. 4,489,455, Spendel, issued Dec. 25, 1984, which involves a washing machine apparatus which contacts fabrics with wash water containing detergent ingredients using a low water:fabric ratio rather than the conventional method of immersing fabrics in an aqueous bath. The compositions herein provide excellent bleaching performance in such mechanical systems. Typically, the ratio of water:fabric ranges from about 0.5:1 to about 6:1 (liters of water:kg of fabric).

EXAMPLE XXVII

Using the machine and operating conditions disclosed in U.S. Pat. No. 4,489,455, cited above, 25 grams of a composition according to Example IV herein are used to launder fabrics with concurrent bleaching. If desired, sudsing of the composition can be minimized by incorporating therein from 0.2% to 2% by weight of a fatty acid, secondary alcohol, or silicone suds controlling ingredient. In the test, all fabrics display significantly improved whiteness after laundering compared with fabrics which have not been exposed to the bleaching system of the invention.

The valerolactam bleach activators are preferably not absorbed onto the peroxygen bleaching compound. To do so in the presence of other organic detergent ingredients could cause safety problems. It has now been discovered that the acyl valerolactam bleach activators of this invention can be dry-mixed with peroxygen bleaching compounds, especially perborate and percarbonate, and thereby avoid potential safety problems. If the valerolactam is a liquid, before dry-mixing, it can be formed into a suitable "particle" using conventional means known in the art.

EXAMPLE XXVIII

A laundry bar suitable for hand-washing soiled fabrics is prepared comprising the following ingredients.

| Component | Weight % |
| --- | --- |
| Linear alkyl benzene sulfonate | 30 |
| Phosphate (as sodium tripolyphosphate) | 7 |
| Sodium carbonate | 20 |
| Sodium pyrophosphate | 7 |
| Coconut monoethanolamide | 2 |
| Zeolite A (0.1–10 microns) | 5 |
| Carboxymethylcellulose | 0.2 |
| Polyacrylate (m.w. 1400) | 0.2 |
| Isononanoyl valerolactam | 5 |
| Sodium perborate tetrahydrate | 10 |
| Brightener, perfume | 0.2 |
| Protease | 0.3 |
| CaSO$_4$ | 1 |
| MgSO$_4$ | 1 |
| Water | 4 |
| Filler* | Balance to 100% |

*Can be selected from convenient materials such as CACO$_3$, talc, clay, silicates, and the like.

A detergent laundry bar is extruded in conventional soap or detergent bar making equipment as commonly used in the art with the bleaching activator dry-mixed with the perborate bleaching compound and not affixed to the surface of the perborate. Testing is conducted following the methods used in Example IV. In the test, fabrics exposed to the bleaching system display significantly improved whiteness after laundering compared with fabrics which have not been exposed to the bleaching system of the invention.

EXAMPLE XXIX

A granular detergent composition is prepared comprising the following ingredients.

| Component | Weight % |
| --- | --- |
| Linear alkyl benzene sulfonate | 20 |
| Phosphate (as sodium tripolyphosphate) | 20 |
| Sodium carbonate | 10 |
| Sodium silicate | 3 |
| Sodium perborate tetrahydrate | 20 |
| Ethylenediamine disuccinate chelant (EDDS) | 0.4 |
| Sodium sulfate | 5.5 |
| 4-nitrobenzoyl valerolactam | 5 |
| Nonanoyloxybenzenesulfonate | 5 |
| Minors, filler** and water | Balance to 100% |

**Can be selected from convenient materials such as CaCO$_3$, talc, clay, silicates, and the like.

Aqueous crutcher mixes of heat and alkali stable components of the detergent compositions are prepared and spray-dried and the other ingredients are dry-mixed so that they contain the ingredients tabulated at the levels shown.

Testing is conducted following the methods used in Example V. In the test, fabrics exposed to the bleaching system display significantly improved whiteness after laundering compared with fabrics which have not been exposed to the bleaching system of the invention.

EXAMPLE XXX

This Example illustrates several liquid bleach compositions in accordance with the invention, all of which are made by the general process described hereinafter. The desired amount of a chelating agent is added to a beaker of water, after which the resulting solution is stirred until the chelating agent is completely dissolved. A phase stabilizer is added to the solution while it is being continuously stirred. Thereafter, the bleach activator and optionally an additional chelating agent is dissolved in the solution. The pH of the solution is adjusted to about 4.0 with an alkaline adjusting agent such as sodium hydroxide.

The following translucent, stable aqueous liquid bleach compositions (Samples A-F) are made as described above, all amounts being expressed as percentages by weight.

TABLE I

|  | Samples | | | | | |
| --- | --- | --- | --- | --- | --- | --- |
|  | A | B | C | D | E | F |
| Water | 81.28 | 81.86 | 82.44 | 83.02 | 78.60 | 83.98 |
| NEODOL 91-10[1] | 10.00 | 10.00 | 10.00 | 10.00 | 10.00 | 10.00 |
| Dipicolinic Acid[2] | 0.05 | 0.05 | 0.05 | 0.05 | 0.05 | 0.05 |
| DEQUEST 2010[3] | 0.05 | 0.05 | 0.05 | 0.05 | 0.05 | 0.05 |
| Nonanoyl Valerolactam | 5.80 | 5.80 | 5.80 | 5.80 | 7.71 | 3.87 |
| Citric Acid | 0.50 | 0.50 | 0.50 | 0.50 | 0.50 | 0.50 |
| NaOH | to pH4 | to pH4 | to pH4 | to pH4 | to pH4 | to pH4 |
| Hydrogen Peroxide | 2.32 | 1.74 | 1.16 | 0.58 | 3.09 | 1.55 |

[1] Alkyl ethoxylate available from The Shell Oil Company.
[2] 2,6-Pyridine dicarboxylic acid commercially available from Aldrich Chemical Co.
[3] Hydroxy-ethylidene diphosphonic acid commercially available from Monsanto Co.

What is claimed is:

1. A laundry bleaching system comprising:
   i) at least about 0.1% by weight of a peroxygen bleaching compound; and
   ii) at least about 0.1% by weight of nonanoyl valerolactam.

2. A laundry detergent composition comprising at least about 0.1% of the bleaching system according to claim 1 and at least about 1% by weight of conventional detergent ingredients.

3. A laundry detergent composition according to claim 2 wherein said conventional detergent ingredients comprise from about 5% to about 80% of a detersive surfactant; said peroxygen bleaching compound is percarbonate or perborate.

4. A laundry detergent composition according to claim 3 wherein said conventional detergent ingredients further comprise a protease enzyme.

5. A laundry detergent composition according to claim 4 further comprising from 0% to about 15% of a second bleach activator.

6. A liquid bleaching system composition comprising:
   a) from about 0.1% to about 10% by weight of a peroxygen bleaching compound comprising hydrogen peroxide or which is capable of yielding hydrogen peroxide in an aqueous solution; and
   b) from about 1% to about 25% by weight of nonanoyl valerolactam.

7. A liquid bleach composition according to claim 6 further comprising from about 1% to about 20% of a nonionic surfactant.

8. A method for cleaning fabrics, said method comprising contacting said fabrics in an aqueous liquor comprising a laundry detergent bleaching effective amounts of a bleaching system according to claim 1.

9. A method for cleaning fabrics in automatic washing machines having parts made of natural rubber which is susceptible to oxidative degradation, said method comprising agitating said fabrics in said machine in an aqueous liquor comprising a laundry detergent bleaching effective amount of a bleaching system according to claim 1 such that said natural rubber parts of said machine are substantially undamaged by the bleaching system.

* * * * *